United States Patent [19]

Glenn

[11] 4,098,290

[45] Jul. 4, 1978

[54] MINIATURE INTERMITTENT POSITIVE PRESSURE BREATHING VALVE

[76] Inventor: Joseph G. Glenn, Rte. 1, Box 1221, Broken Arrow, Okla. 74012

[21] Appl. No.: 746,736

[22] Filed: Dec. 2, 1976

[51] Int. Cl.² ............... A61M 15/00; A62B 7/02
[52] U.S. Cl. ..................... 137/604; 128/145.6; 128/209
[58] Field of Search ............ 137/604; 128/145.5, 128/145.6, 145.8, 209, 210

[56] References Cited

U.S. PATENT DOCUMENTS

| 3,319,627 | 5/1967 | Widsor | 128/145.8 X |
| 3,603,308 | 9/1971 | Spralding | 128/145.8 |
| 3,653,379 | 4/1972 | Glenn | 128/145.6 |
| 3,768,962 | 10/1973 | Baranowski | 137/604 X |
| 3,881,480 | 5/1975 | Lafourcade | 128/145.8 |

Primary Examiner—Robert G. Nilson
Attorney, Agent, or Firm—Head, Johnson & Chafin

[57] ABSTRACT

A miniature intermittent positive pressure breathing valve designed for use with constant pressure sources, having readily interchangeable orifice components for varying respiratory flow pressures.

4 Claims, 4 Drawing Figures

4,098,290

MINIATURE INTERMITTENT POSITIVE PRESSURE BREATHING VALVE

BACKGROUND OF THE INVENTION

The proper treatment of numerous pulmonary disorders and in particular, the treatment of chronic bronchitis and pulmonary emphysema often requires that the afflicted patient receive external breathing assistance to improve alveolar ventilation and reduce ventilatory work. In such treatment, the use of intermittent positive pressure breathing (IPPB) equipment has proven effective and also provides an efficient delivery system for medications employed in treatment such as decongestants, mucolytics, and bronchodialators.

A typical present-day manual respiration system suitable for home or clinic use comprises a venturi tube in combination with a nebulizer. Compressed gas is fed through the throat of the venturi by means of a nozzle. Apertures in the venturi tube body in open communication with the atmosphere permit air to be entrained with the flow of compressed gas through the venturi tube in accordance with Bernoulli's principle. In typical operation, the combined flow of gas and entrained air exiting from the venturi at a slight positive pressure enters a nebulizer chamber for mixing with atomized medication prior to inhalation by the patient. A finger controlled by-pass vent, open to the atmosphere, which has a significantly larger flow capacity than the nozzle, is connected to the compressed gas line, and opening of the vent effectively stops flow through the nozzle, allowing the patient to exhale against negligible back pressure. The exhaled gases return through the venturi tube and pass into the room via the apertures in the venturi tube body.

With sources of constant pressure gas, it becomes apparent that the pressure to the patient's lungs remains constant during inhalation. However, as patients may be afflicted with various pulmonary disorders, the desired lung pressure may also vary for proper treatment. In view of this need, adjustable pressure IPPB ventilators have been designed, such as the one disclosed in U.S. Pat. No. 3,653,379, issued to Joseph G. Glenn. The aforementioned patent discloses a venturi tube having a slidable nozzle. By varying the nozzle position with respect to the venturi throat, changes in the downstream pressure are effected without need for regulation of the inlet pressure. While effective, such apparatus is relatively expensive to manufacture, and this additional cost is passed on to the patient, who may need no more than one lung pressure setting.

As most respirators are hand-held, it is necessary that the weight of the device be minimized Furthermore, the IPPB valves presently available are difficult to sterilize and create cross-contamination problems.

It is therefore an object of this invention to provide an IPPB valve which may be readily adapted for varying lung pressure requirements of the individual patient, be lightweight for the convenience of the user, and be sufficiently inexpensive to be used on a disposable basis.

SUMMARY OF THE INVENTION

The present invention contemplates a miniature intermittent positive pressure breathing valve apparatus designed to permit control over a patient's inspiratory flow pressure and flow rate in accordance with the treatment prescribed by his physician. Simplicity of the design and the use of inexpensive construction materials permit manufacture of the apparatus for use on a disposable basis.

The IPPB valve apparatus comprises an annular body providing a substantially cylindrical chamber and having a plurality of circumferentially spaced apertures therein; a plug member mounted to the end of the annular body upstream from the circumferential openings having an inlet bore means for receiving compressed gas in the upstream end thereof and a centrally disposed axial jet orifice in the downstream end thereof in open communication with the interior of the cylindrical chamber and with said inlet bore means; and a hollow cylindrical cap member sealably mounted to the end of the annular body downstream from the circumferentially spaced apertures providing a baffle wall across the end of the annular body having a centrally disposed axial port.

In operation, a source of compressed gas or air is connected to the plug member inlet bore means, such as by flexible tubing. The flow of compressed gas through the orifice into the cylindrical chamber induces a flow of room air through the circumferential apertures into the chamber. The compressed gas flowing through the orifice and the aspirated room air exit the cylindrical chamber through the axial port in the baffle wall provided by the end cap member. Interchangeable cap members having different port diameters may be selected in calibrated sizes for the respiratory flow rates and pressure needs of the individual patient. In exhaling, the compressed air flow through the plug member orifice is bypassed by means of a manually opened vent in the compressed gas line, and the patient may exhale with negligible back pressure.

In one modification of the invention, a relief valve is installed in the compressed gas line leading to the plug member inlet bore means as a safety precaution against over-pressuring the valve apparatus.

In a second modification, the annular body is sealed from the atmosphere by a housing providing a second chamber in open communication with the cylindrical chamber provided by the annular body through the circumferentially spaced apertures. Said housing provides an inlet means for the supply of additional oxygen to said second chamber and a check valve is located in the housing wall to permit flow from the second chamber to the atmosphere.

DETAILED DESCRIPTION OF THE PREFERRED EMBODIMENTS

Figure 1:
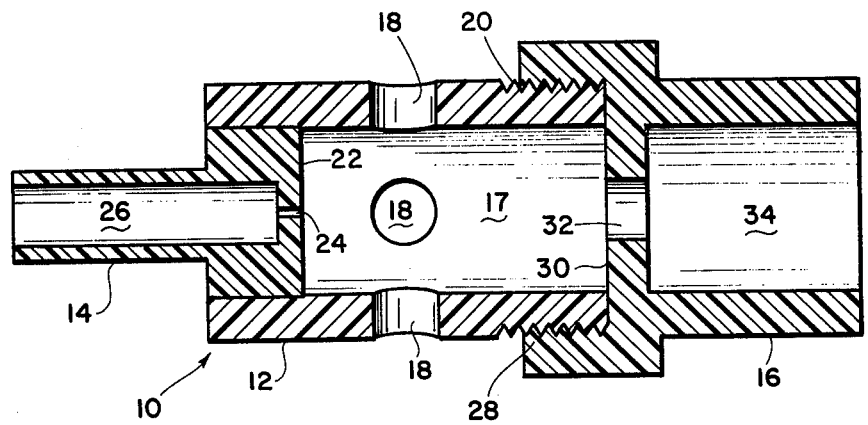
FIG. 1 is an enlarged sectional view of one embodiment of the invention.

Referring to the drawings in detail, and in particular to FIG. 1 thereof, reference character 10 generally indicates a miniature IPPB valve. The valve comprises an annular body 12, plug member 14, and cap member 16.

Annular body 12 provides a cylindrical chamber 17 and has a plurality of circumferentially spaced apertures 18, preferably centered in a common plane perpendicular to the annular body axis and approximately equi-distant from the ends of the body. The outer periphery of the downstream portion 20 of annular body 12 is shown threaded in FIG. 1 for coupling with cap member 16, although any suitable means for providing a sealable removable coupling between the annular body and the cap member would suffice.

Plug member 14 is cylindrically shaped, having a downstream end diameter sized so as to form an inner periphery seal with the interior walls of the annular body 12, and the plug member 14 may be secured to said walls upstream from apertures 18 in any suitable manner. The upstream end of plug member 14 extends beyond the upstream end of annular body 12 and is provided with an inlet bore 26 for receiving compressed gas. The downstream end 22 of plug 14 is provided with an axial jet orifice 24, centrally disposed therein, in open communication with the cylindrical chamber 17 and the inlet bore 26.

The cap member 16 is connected to the downstream end of annular body 18 by means of a threaded female fitting 28. Said cap member includes a baffle wall 30 perpendicular to the axis of the annular body 12, having a centrally disposed axial port 32 in open communication with cylindrical chamber 17. The downstream portion of cap member 16 is cylindrical in shape for insertion into the wall of a nebulizer (not shown) and provides a cylindrical conduit 34 in open communication with the axial port 32.

Compressed gas introduced to the inlet bore 26 of plug member 14 by means of a compressed gas line (not shown) passes through orifice 24 into the cylindrical chamber 17. In accordance with Bernoulli's principle, room air is aspirated through apertures 18 into chamber 17, and the combined flow passes through axial port 32 provided by the baffle wall 30. A finger controlled bypass vent (not shown) located in the compressed gas line may be opened during expiration, and the exhaled gases pass through axial port 32 and into the room via apertures 18. Construction of the valve as disclosed results in overall dimensions of the IPPB valve of approximately 1⅜inches in overall length and 1 inch in overall diameter.

Figure 2:
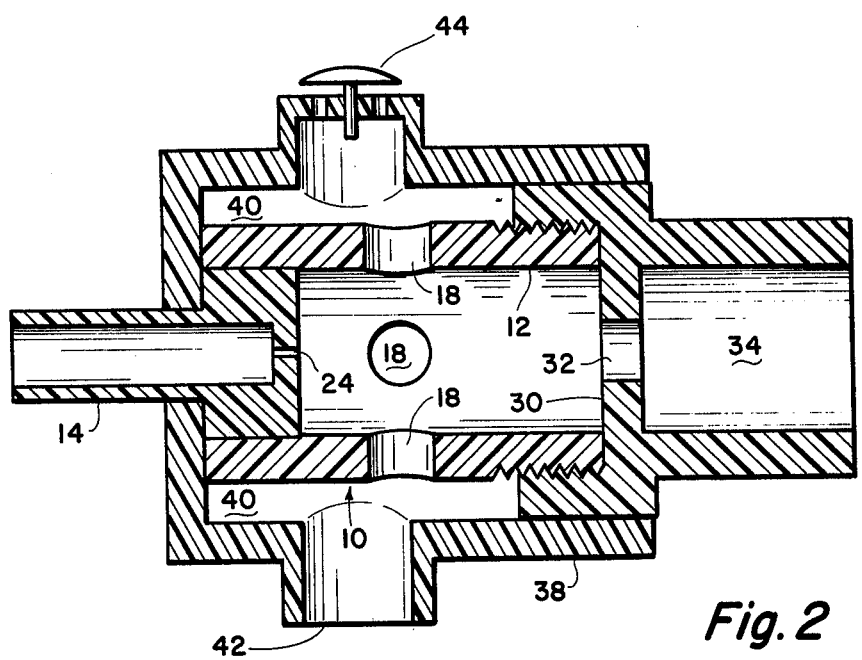
FIG. 2 is an enlarged sectional view of the invention as modified for providing additional oxygen to the patient.

In a modification of the apparatus shown in FIG. 2 of the drawings, the IPPB valve 10 is jacketed with a housing 38 providing a chamber 40 surrounding the annular body 12 and having an inlet passageway 42. The housing jacket is also provided with a check valve 44 which permits gas to pass from the housing chamber 40 to the atmosphere. This modification permits concentration of the oxygen supply to the patient by passing oxygen through the inlet passageway 42 to the housing 40. The oxygen contained in chamber 40 is then aspirated through the apertures 18 during inhalation.

Figure 3:
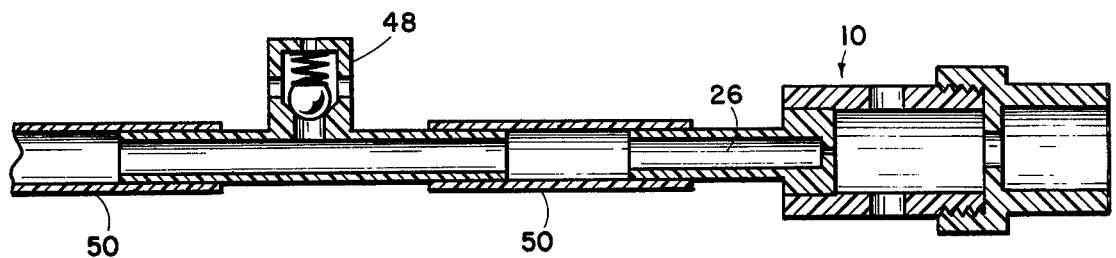
FIG. 3 is a cross-sectional view of the invention showing the valve proper in combination with a safety relief valve.

FIG. 3 of the drawing shows the IPPB valve 10 in combination with a safety relief valve 48 inserted in a compressed gas line 50 leading to the inlet 26 of the IPPB valve. If the apparatus is inadvertently connected to a pressure source operating above normal level, valve 48 opens, and the gas is vented to the atmosphere, preventing harm from occurring to the downstream equipment or patient.

Figure 4:
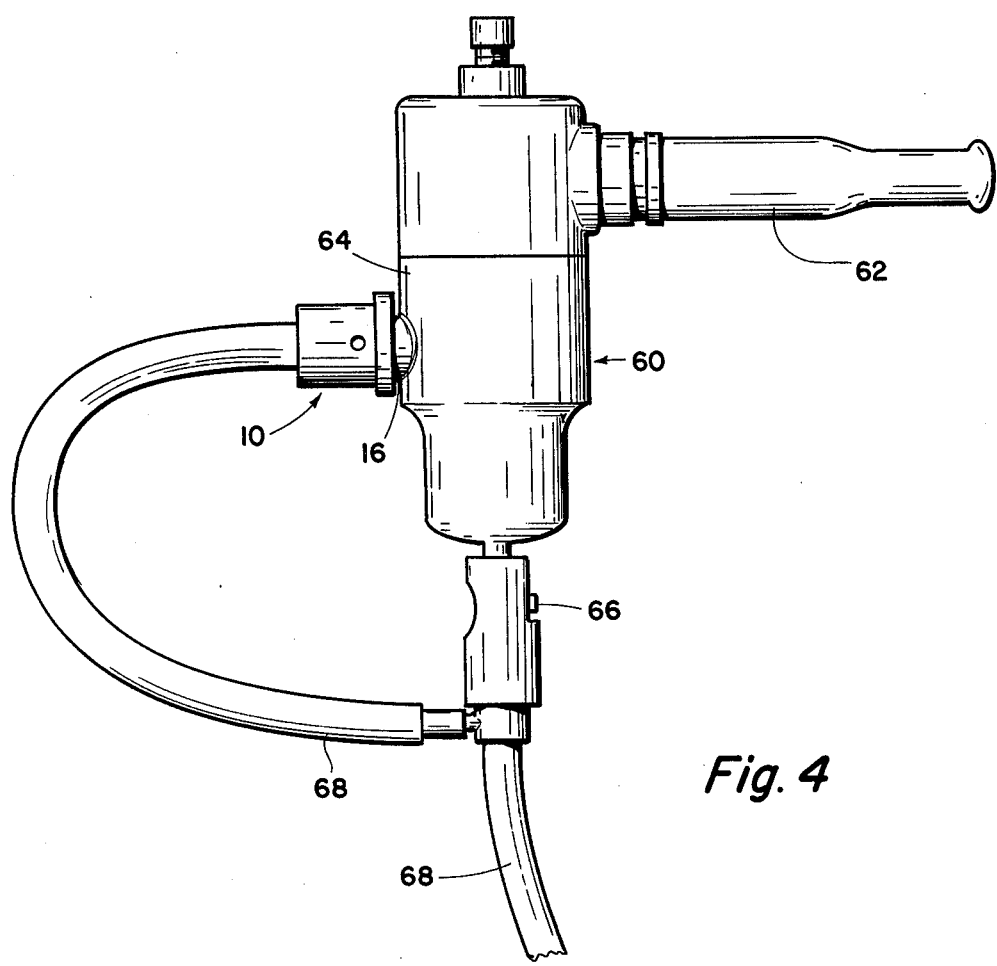
FIG. 4 is a drawing of the valve in combination with a hand-held nebulizer.

FIG. 4 is a drawing showing the IPPB valve 10 in combination with a nebulizer generally indicated by reference character 60, and mouthpiece 62. As shown therein, the downstream end of cap member 14 is inserted into the housing wall 64 of neubilizer 60. The housing wall 64 provides a chamber (not shown) wherein air from the IPPB valve is mixed with vaporized medication prior to entering mouthpiece 62. A finger controlled bypass vent opening 66 is provided in the compressed gas line 68 for relieving back pressure during exhalation.

Whereas the present invention has been described in particular relation to the drawings attached hereto, it should be understood that other and further modifications, apart from those shown or suggested herein may be made within the spirit and scope of this invention.

What is claimed is:

1. A miniature IPPB valve apparatus, which comprises:
    an annular body, providing a substantially cylindrical chamber and having a plurality of circumferentially spaced apertures;
    a plug member sealably mounted to one end of the annular body forward of the circumferentially spaced apertures, said plug member having an inlet bore means for receiving compressed gas in the one end thereof and a centrally disposed axial jet orifice in the opposite end thereof, in open communication with the interior of the cylindrical chamber and said inlet bore means; and
    a hollow cylindrical cap member sealably mounted in substantially axial alignment to the opposite end of the annular body, providing a baffle wall across the end of said annular body, said baffle wall having a centrally disposed axial port, said cylindrical cap member being interchangeable with other cap members having axial ports of varying sizes.

2. A miniature IPPB valve apparatus, as recited in claim 1, further comprising:
    a tube sealably secured to the plug member in substantial alignment with the inlet bore means for transferring compressed gas thereto; and
    a high-pressure relief valve means operably connected to the tube for relieving pressure to the atmosphere above a pre-set level.

3. A miniature IPPB valve apparatus, as recited in claim 1, further comprising:
    means for providing additional oxygen to the annular body cylindrical chamber.

4. A miniature IPPB valve apparatus as recited in claim 3, wherein the means for providing additional oxygen to the annular body cylindrical chamber comprises:
    a housing, providing a sealed chamber surrounding the annular body, having an inlet duct for supplying additional oxygen to the interior of the housing chamber, and
    a check valve means in the housing wall for permitting the transfer of gas from the housing chamber to the atmosphere.

* * * * *